United States Patent [19]

Ochi et al.

[11] 4,415,573
[45] Nov. 15, 1983

[54] NOVEL URACIL DERIVATIVES, PROCESS FOR PREPARING THE SAME AND A PHARMACEUTICAL COMPOSITION CONTAINING THE SAME

[75] Inventors: Kiyoshige Ochi, Kawagoe; Katsuhito Miyamoto, Tokyo; Hiroki Mitsui, Iruma; Yumiko Tsuruma; Isao Matsunaga, both of Tokyo; Takashi Matsuno, Omiya; Shigeru Takanashi, Asaka; Minoru Shindo, Tokyo, all of Japan

[73] Assignee: Chugai Seiyaku Kabushiki Kaisha, Tokyo, Japan

[21] Appl. No.: 291,847

[22] Filed: Aug. 10, 1981

[30] Foreign Application Priority Data

Aug. 19, 1980 [JP] Japan ................................ 55-112993

[51] Int. Cl.³ .................... A61K 31/505; C07D 239/10
[52] U.S. Cl. .................................... 424/251; 544/311;
544/312; 544/313; 544/314; 542/468
[58] Field of Search ............... 424/251; 544/311, 312, 544/313, 314; 542/468

[56] References Cited

U.S. PATENT DOCUMENTS 4,122,251  10/1978  Misaki et al. ...................... 536/23

OTHER PUBLICATIONS

*Chemical Abstracts*, vol. 94, No. 21, Jun. 2, 1981, p. 723, Abstract No. 175027g, Karpeiskii, M. Ya. et al.
*J. Med. Chem.*, vol. 24, No. 6, Jun. 8, 1981, pp. 753–756, Kelley, J. L. et al.
*J. Biol. Chem.*, vol. 253, No. 24, 1978, pp. 8721–8727, Fyfe, J. A. et al.

*Primary Examiner*—Donald B. Moyer
*Assistant Examiner*—Frederick W. Pepper
*Attorney, Agent, or Firm*—Browdy and Neimark

[57] ABSTRACT

Novel uracil derivatives of the formula

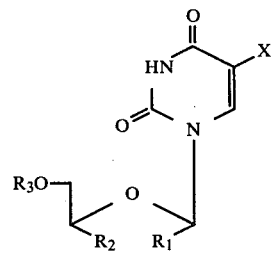

(wherein $R_1$, $R_2$ $R_3$ and X are defined in the description) and their pharmaceutically acceptable salts, process for preparing the same and pharmaceutical composition containing the same are disclosed. The uracil derivatives have good antitumor activity and, therefore, are useful as antitumor preparation.

10 Claims, No Drawings

NOVEL URACIL DERIVATIVES, PROCESS FOR PREPARING THE SAME AND A PHARMACEUTICAL COMPOSITION CONTAINING THE SAME

This invention relates to a novel uracil derivative having good antitumor activity. More particularly, this invention relates to an uracil derivative of the formula

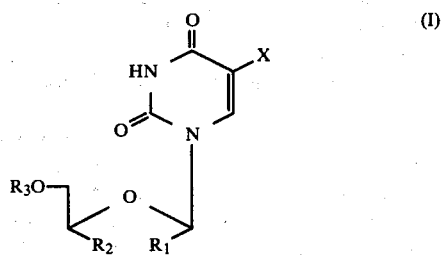

wherein $R_1$ is a hydrogen atom, an alkyl group, a cycloalkyl group or

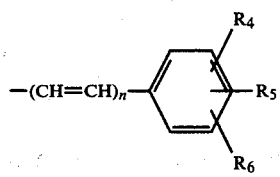

(wherein n is 0 or 1; $R_4$, $R_5$ and $R_6$ are the same or different and mean a hydrogen atom, an alkyl group, an alkoxy group, an alkenyloxy group, a hydroxy group, an acyloxy group, a halogen atom or a nitro group; and two of $R_4$, $R_5$ and $R_6$ may be taken together to form an alkylene dioxy group); $R_2$ is a hydrogen atom or an alkyl group; $R_3$ is a hydrogen atom, an acyl group, an unsubstituted or alkylsubstituted phenylsulfonyl group or an alkylsulfonyl group; and X is a hydrogen atom, a halogen atom or an alkyl group which may be substituted with one or more halogen atom(s).

The alkyl group for $R_1$ in the formula (I) is a straight or branched chain alkyl group having from 1 to 14 carbon atoms. Examples of such alkyl group are methyl, ethyl, propyl, isopropyl, butyl, isobutyl, pentyl, isopentyl, hexyl, isohexyl, octyl, nonyl, decyl, undecyl, dodecyl and tetradecyl.

The "cycloalkyl group" for $R_1$ has from 3 to 8 carbon atoms and are, for example, cyclopropyl, cyclobutyl, cyclopentyl, cyclohexyl, cycloheptyl, and cyclooctyl.

The "alkyl group" for $R_4$, $R_5$ and $R_6$ contains from 1 to 5 carbon atoms and is a straight or branched chain alkyl group, for example, methyl, ethyl, propyl, isopropyl, butyl, isobutyl, pentyl and isopentyl.

The "alkoxy group" for $R_4$, $R_5$ and $R_6$ includes a straight or branched chain alkoxy group containing from 1 to 6 carbon atoms, examples of which are methoxy, ethoxy, propoxy, isopropoxy, butoxy, isobutoxy, pentyloxy and hexyloxy.

The "acyloxy group" for $R_4$, $R_5$ and $R_6$ contains from 2 to 4 carbon atoms and includes, for example, an aliphatic acyloxy group such as acetyloxy, propionyloxy and butyryloxy.

The halogen atom for $R_4$, $R_5$ and $R_6$ or X is fluorine, chlorine, bromine or iodine.

The "alkylene dioxy group" which may be formed by taking two of $R_4$, $R_5$ and $R_6$ is preferably a methylene dioxy group.

The "alkyl group" for $R_2$ is straight or branched chain alkyl having from 1 to 5 carbon atoms, and includes, for example, methyl, ethyl, propyl, isopropyl, butyl, isobutyl, pentyl and isopentyl.

The "acyl group" for $R_3$ is straight or branched alkanoyl having from 1 to 5 carbon atoms, and includes, for example, formyl, acetyl, propionyl, butyryl, isobutyryl, valeryl, isovaleryl and pivaloyl.

The "alkyl-substituted or unsubstituted phenylsulfonyl group" for $R_3$ includes, for example, p-toluenesulfonyl, p-ethylbenzenesulfonyl and benzenesulfonyl.

The "alkylsulfonyl group" for $R_3$ includes lower alkylsulfonyl such as methylsulfonyl, ethylsulfonyl and propylsulfonyl.

The alkyl group for X is a straight or branched chain alkyl having from 1 to 4 carbon atoms which may be substituted with halogen atom(s) such as fluorine, chlorine or bromine. Examples of this alkyl group are methyl, ethyl, propyl, isopropyl, butyl, isobutyl and trifluoromethyl.

The halogen atom for X means fluorine, chlorine, bromine or iodine.

Some of the object compounds of this invention have an asymmetric carbon atom and are usually prepared as a racemic mixture. The racemic mixture can be resolved by a conventional method, if desired, to give each epimer. These optical isomers are involved in the object compounds of this invention.

According to this invention, the compound of the formula (I) is prepared by reacting an acetal of the formula (II)

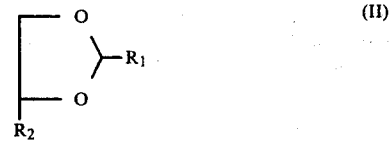

(wherein $R_1$ and $R_2$ are as defined above) with an uracil derivative of the formula (III)

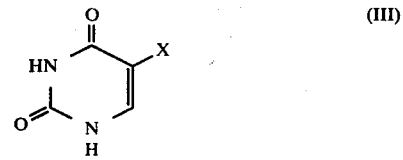

(wherein X is as defined above) or its trialkylsilyl ether derivative in the presence of a Lewis acid, and then acylating the product if the object compound of the formula (I) wherein $R_3$ is an acyl group is desired.

The starting compound of the formula (II)

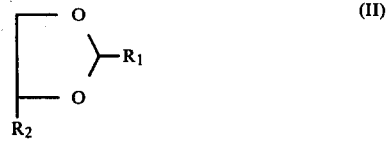

(wherein $R_1$ and $R_2$ are as defined above) can be easily prepared by dehydration condensation of an aldehyde of the formula R₁CHO with a substituted ethylene glycol in the presence of an acid catalyst.

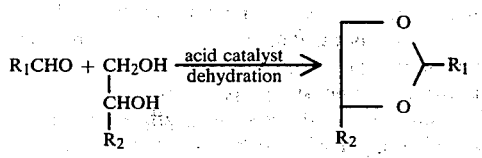

(wherein R₁ and R₂ are as defined above) The acid catalyst which can be used in the above condensation reaction includes, preferably, organic acids such as p-toluenesulfonic acid and methanesulfonic acid; inorganic acids such as hydrochloric acid and sulfuric acid; and strongly acidic ionexchange resins such as Amberlite IR-120 (manufactured by Rohm and Haas Co.) and Amberlist 15 (manufactured by Rohm and Haas Co.).

The uracil derivative of the formula (III)

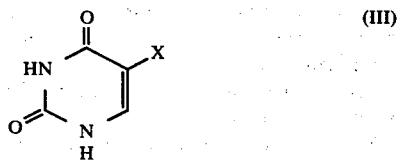

(III)

(wherein X is as defined above) is a well-known compound and can be easily prepared by a conventional way. Thus, no further explanation on the preparation is needed.

Examples of the uracil derivatives (III) are uracil, 5-fluorouracil, 5-bromouracil, 5-iodouracil, 5-methyluracil, 5-ethyluracil, and 5-trifluoromethyluracil, and bis-trimethylsilyl ether thereof.

The solvent which is useful in the reaction is one capable of dissolving the acetal of the formula (II), the uracil derivative of the formula (III) or its bis-trimethylsilyl ether, and the Lewis acid catalyst without decomposition. Examples of the preferred solvent are dichloromethane, chloroform, dimethylformamide and dimethylacetamide.

The Lewis acids which are useful as the acid catalyst are preferably anhydrous stannic chloride, titanium tetrachloride, boron trifluoride, zinc chloride, aluminum chloride, and ethylalminum chloride. The acid catalyst is usually used in an amount of from 0.1 to 10 moles, preferably from 0.1 to 1.0 moles per mole of the uracil derivative of the formula (III).

The reaction is usually carried out at a temperature of from −10° to 100° C. for 0.5 to 50 hours, preferably at 20° to 50° C. for 1 to 12 hours. The reaction conditions varies mainly depending on the amount of the acid catalyst used. For example, the reaction will be completed at room temperature in a few hour if the excess catalyst is used.

The object compounds of this invention represented by the formula (I) wherein R₃ is an acyl group can be prepared by acylating a compound of the formula (I) wherein R₃ is a hydrogen atom with use of a conventional acylating agent. Acylating agents which can be used for this acylation include, preferably, acid anhydrides such as acetic anhydride, propionic anhydride and butyric anhydride, and acid chlorides such as acetyl chloride, propionyl chloride and butyryl chloride. Although the acylating agent may be used alone, the use of a tertially amine such as pyridine, triethylamine or dimethylaniline as an acid acceptor is preferred.

The solvents which are useful in the acylating reaction are those capable of dissolving the hydroxy form of the compound represented by the formula (I), and of not inhibiting the reaction. Examples of the preferred solvents are pyridine, dichloromethane, chloroform and tetrahydrofuran. The acylation reaction is carried out at a temperature of from below 0° C. to room temperature, and if pyridine is used as the solvent, the reaction will be completed at room temperature for about 3 hours. The isolation and purification of the object compound of this invention can be easily effected by a conventional manner.

For example, the reaction mixture may be treated with methanol to remove the silyl group from the product, and the solvent is evaporated off after removing a catalyst. The residure is then dissolved in an organic solvent such as chloroform, dichloromethane or ethyl acetate, and after removing the catalyst, washed with an aqueous sodium chloride solution. The organic solution is dried over a desiccant such as anhydrous sodium sulfate or magnesium sulfate, and the solvent evaporated off to give a crude product.

Alternatively, the catalyst is removed as precipitate from the reaction mixture by adding to the mixture an alcohol such as methanol and an inorganic base such as sodium bicarbonate, sodium carbonate or sodium hydroxide, and the solvent is evaporated off to give a crude product. The crude product is purified by column chromatography with silica gel or almina by a conventional method to give a purified product.

The product, the object compound of this invention represented by the formula (I) exhibits strong antitumor activity and, therefore, is useful as an antitumor agent.

The object compound of this invention is formulated by a conventional pharmaceutical technique into tablet, granule, powder, capsule or injection which is administered to a patient orally or parenterally. Diluents for formulating tublet, granule, powder or capsule are lactose, starch, dextrin, sucrose, crystalline cellulose, kaolin, calcium carbonate, talc and magnesium stearate. Diluents preferably used for injection are distilled water or an aqueous solution of a salt such as sodium chloride or potassium chloride.

The dosage per day is usually: from 50 to 2,000 mg/day, preferably from 100 to 1,500 mg/day for oral administration, and usually from 50 to 2,000 mg/day, preferably from 100 to 1,500 mg/day for injection. The desired daily dosage of the formulation is administered either at one time or in several doses.

EXPERIMENT 1

Male CDF₁ mice (6 weeks old) divided into groups of 6 members each were intraperitoneally inoculated P388 leukemic cells in a count of 10⁶ cells/head. Twenty four hours after the inoculation, the active compound of this invention was dissolved or suspended in a physiological saline or a 0.25% carboxymethylcellulose aqueous solution and administered intraperitoneally (i.p.) or orally (p.o.) in a dose as defined in Table 1 below once a day for 5 days.

The antitumor activity of each of the test compounds was evaluated in terms of percent ILS.

$$ILS\ \% = \frac{\text{Average survival days of the administered group at a predetermined dose level}}{\text{Average survival days of the control group}} \times 100$$

TABLE 1

Antitumor Activity of Compounds of this Invention against P388 Leukemic Cells

| Test Compounds (Example No.) | Daily Dosage (mg/kg) | ILS % i.p. | ILS % p.o. |
|---|---|---|---|
| 9 | 12.5 | 50 | — |
|  | 25 | 58 | 2 |
|  | 50 | 63 | 13 |
|  | 100 | 84 | 46 |
| 10 | 25 | 33 | — |
|  | 50 | 56 | 6 |
|  | 100 | 70 | 20 |
|  | 200 | — | 36 |
| 11 | 50 | 23 | 7 |
|  | 100 | 40 | 18 |
|  | 200 | 69 | 37 |
| 13 | 6.25 | 29 | — |
|  | 12.5 | 42 | — |
|  | 25 | 54 | — |
|  | 50 | 70 | 10 |
|  | 100 | — | 28 |
|  | 200 | — | 54 |
| 15 | 6.25 | 29 | — |
|  | 12.5 | 36 | — |
|  | 25 | 53 | — |
|  | 50 | 62 | 5 |
|  | 100 | 92 | 28 |
|  | 200 | — | 47 |
| 25 | 50 | 29 | 6 |
|  | 100 | 42 | 21 |
|  | 200 | 53 | 41 |
| 31 | 50 | 24 | 5 |
|  | 100 | 33 | 13 |
|  | 200 | 53 | 25 |
| 32 | 50 | 10 | 8 |
|  | 100 | 26 | 19 |
|  | 200 | 45 | 44 |
| 34 | 50 | 90 | — |
|  | 100 | 102 | 5 |
|  | 200 | 138 | 29 |
| 1-(2-tetrahydrofuryl)-5-fluorouracil | 50 | 7 | 2 |
|  | 100 | 24 | 21 |
|  | 200 | 39 | 41 |
|  | 300 | died | died |
| 5-fluorouracil | 2.5 | 16 | — |
|  | 5 | 45 | 3 |
|  | 10 | 61 | 5 |
|  | 20 | 81 | 29 |
|  | 30 | died | 33 |

EXPERIMENT 2

The antitumor activity of some additional compounds of this invention was determined as in Experiment 1. The results are shown in Table 2 below.

TABLE 2

Antitumor Activity against P388 Leukemic Cells

| Test Compounds (Example No.) | Daily Dosage (mg/kg) | ILS (%) i.p. |
|---|---|---|
| 45 | 50 | 62 |
| 46 | 100 | 86 |
| 56 | 100 | 89 |
| 57 | 100 | 75 |
| 58 | 100 | 57 |
| 59 | 100 | 57 |
| 5-fluorouracil | 10 | 69 |
| 1-(2-tetrahydrofuryl)-5-fluorouracil | 100 | 41 |

EXPERIMENT 3

A Colon 26 or Lewis lung carcinoma tumor piece (1 mm$^3$) was subcutaneously inoculated in the side belly of a test mouse. CDF$_1$ strain male mice (6-7 weeks old) and BDF$_1$ strain male mice (6-7 weekas old) were used as host mice for Colon 26 tumor and Lewis lung carcinoma, respectively. Three days after the inoculation, the mice which were confirmed to have taken the tumor piece in their tissue were divided into groups of 6-8 heads each, and each mouse was orally administered once a day for 5 days with a suspension or solution of the predetermined amount of test compound in a 0.25% CMC aqueous solution in a dose of 0.1 ml/10 g body weight. Twenty one days after the inoculation, the tumor was taken out and the wet weight of each tumor was measured, and growth inhibition ratio (% GIR) was determined.

The % GIR was calculated by the following equation $$\%\ GIR = \frac{C - T}{C} \times 100$$

wherein T is the average tumor weight of a group administered the test compound, and C is the average tumor weight of the control group.

The results are shown in Table 3 below.

TABLE 3

Antitumor Activity against Solid Tumor Colon 26 and Lewis lung Carcinoma

| Test Compounds (Example No.) | Colon 26 Daily dosage (mg/kg) | Colon 26 GIR (%) | Lewis lung car. Daily dosage (mg/kg) | Lewis lung car. GIR (%) |
|---|---|---|---|---|
| 10 | 200 | 98 | 200 | 87 |
| 11 | 200 | 94 | 200 | 87 |
| 12 | 100 | 80 | 200 | 83 |
| 16 | 100 | 27 | 200 | 73 |
| 34 | 200 | 38 | 200 | 47 |
| 45 | 100 | 56 | 200 | 75 |
| 46 | 100 | 21 | 200 | 68 |
| 47 | 300 | 67 | 300 | 89 |
| 54 | 200 | 62 | 200 | 83 |
| 55 | 300 | 62 | 300 | 50 |
| 56 | 300 | 54 | 300 | 25 |
| 57 | 300 | 84 | 300 | 84 |
| 58 | 300 | 56 | 300 | 29 |
| 59 | 200 | 48 | 300 | 64 |
| 60 | 300 | 75 |  |  |
| 5-fluorouracil | 30 | 49 | 40 | 83 |
| 1-(2-tetrahydrofuryl)-5-fluorouracil | 200 | 79 | 200 | 84 |

Preparation of the compounds of this invention is described in detail by reference to the following Examples which are given here for illustrative purpose only.

EXAMPLE 1

5-Fluorouracil (5-FU) (10 g) was refluxed in hexamethyldisilazane (40 ml) for 5 hours and, after evaporating off excess hexamethyldisilazane, the resulting bis(trimethylsilyl)-5-fluorouracil was dissolved in dried chloroform. To the solution was added 1,3-dioxolane (10 ml) and then was added dropwise a solution of anhydrous stannic chloride (6.2 ml) in chloroform (15 ml) at room temperature for one hour. After completion of the addition, the reaction was effected at room temperature for 30 minutes, and the reaction mixture was added to a methanol (200 ml) containing sodium bicarbonate (30 g)

and stirred for one hour. The precipitate was removed by filtration and the filtrate was evaporated. The residue was treated with a small amount of methanol to give 3 g of crystalline 1-(2-hydroxyethoxy)methyl-5-fluorouracil.

m.p.: 153.5°–155° C. (recrystallized from methanol)

NMR (DMSO-d$_6$)δ: 7.98 (1H,d,H-6), 4.98 (2H,S,OCH$_2$$\overset{O}{\underset{N}{<}}$), 3.47 (4H,bs,HOCH$_2$CH$_2$O—).

EXAMPLE 2

1-(2-Hydroxyethoxy)methyl-5-fluorouracil (1 g) prepared in Example 1 was dissolved in a mixture of acetic anhydride (5 ml) and pyridine (5 ml) and the solution was stirred at room temperature for 3 hours. The reaction mixture was poured into ice-water and the resulting oil was extracted with chloroform (30 ml). The extract was washed with hydrochloric acid, aqueous sodium bicarbonate and then water, dried over magnesium sulfate and the solvent was evaporated off under reduced pressure. The residue was treated with methanol to give 0.9 g of crystalline 1-(2-acetoxyethoxy)methyl-5-fluorouracil.

m.p.: 145°–146.5° C. (recrystallized from methanol)

NMR (CDCl$_3$ + DMSO-d$_6$)δ: 7.77 (1H,d,H-6), 5.11 (2H,

S,CH$_2$$\overset{O}{\underset{N}{<}}$), 4.30–4.04 (2H,m,CH$_3$COOCH$_2$CH$_2$O), 3.92–3.64 (2H,m,CH$_3$COOCH$_2$CH$_2$O), 2.02 (3H,S,CH$_3$COO).

EXAMPLE 3

1-(2-Hydroxyethoxy)methyl-5-fluorouracil (1 g) obtained in Example 1 was dissolved in pyridine (5 ml) and to the solution was added p-toluenesulfonylchloride (1.12 g) under cooling in an ice bath, and then the mixture was stirred at room temperature for 1.5 hours. After completion of the reaction, the mixture was poured into ice-water and the resulting oil was extracted with chloroform (30 ml). The chloroform layer was washed with hydrochloric acid and then with water, and dried over magnesium sulfate to give crystalline 1-(2-p-toluenesulfonyloxyethoxy)methyl-5-fluorouracil (1.2 g).

m.p.: 141°–142.5° C.

NMR (DMSO-d$_6$)δ: 7.97 (1H,d,H-6), 7.55 (4H,q,CH$_3$

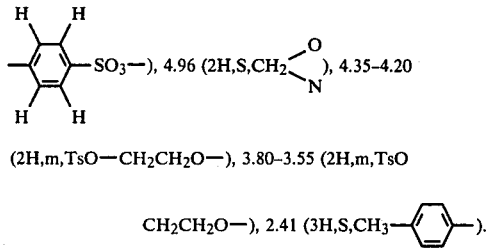

(2H,m,TsO—CH$_2$CH$_2$O—), 3.80–3.55 (2H,m,TsO

CH$_2$CH$_2$O—), 2.41 (3H,S,CH$_3$—⟨⟩—).

EXAMPLE 4

5-Fluorouracil (10 g) was refluxed in hexamethyldisilazane and, after distilling off excess hexamethyldisilazane, the resulting bis(trimethylsilyl)-5-fluorouracil ether was dissolved in chloroform (50 ml). After addition of 2-methyl-1,3-dioxolan (1.0 ml), a solution of stannic chloride (6 ml) in chloroform (15 ml) was added dropwise to the reaction mixture for one hour while stirring at room temperature. After stirring for 30 minutes, the reaction mixture was poured into 50% aqueous methanol (100 ml) containing sodium bicarbonate (24 g) while vigorously stirring. The precipitate was removed by filtration, and the filtration was evaporated under reduced pressure. The residue was purified by column chromatography to give 5 g of 1[1-(2-hydroxyethoxy)ethyl]-5-fluorouracil.

m.p.: 118°–120° C.

NMR (CD$_3$OD)δ: 7.78 (1H,d,H-6), 6.0–5.6 (1H,q,CH$_3$CH$\overset{O}{\underset{N}{<}}$), 3.8–3.4 (4H,m,HOCH$_2$CH$_2$O—), 1.44 (3H,d,CH$_3$CH$\overset{O}{\underset{N}{<}}$).

EXAMPLE 5

1-[1-(2-Hydroxyethoxy)ethyl]-5-fluorouracil (2 g) obtained in Example 2 was treated with acetic anhydride and pyridine as in Example 2 to give 2 g of 1-[1-(2-acetoxyethoxy)-ethyl]-5-fluorouracil.

m.p.: 121°–122° C. (recrystallized from aqueus methanol)

NMR (CDCl$_3$)δ: 7.44 (1H,d,H-6), 5.88 (1H,q,CH$_3$CH$\overset{O}{\underset{N}{<}}$), 4.1–4.45 (2H,m,CH$_3$COOCH$_2$CH$_2$O—), 3.58–3.85

(2H,m,CH$_3$COOCH$_2$CH$_2$O—), 2.07 (3H,S,CH$_3$COO—), 1.49 (3H,d,CH$_3$CH$\overset{O}{\underset{N}{<}}$).

EXAMPLE 6

Bis(trimethylsilyl)-5-fluorouracil which had been prepared by treating 5-fluorouracil (10 g) as in Example 1 was dissolved in chloroform (20 ml). Separately prepared 2-ethyl-1,3-dioxolan (15 ml) from propionyldehyde (25 ml) and ethylene glycol (25 ml) was added to the above solution. Then, to the mixture was added dropwise a solution of anhydrous stannic chloride (6 ml) in chloroform (15 ml) under cooling in an ice bath for one hour. Following stirring at room temperature for one hour, the reaction mixture was poured into methanol (100 ml) containing sodium bicarbonate (30 g) and, after removing the resulting precipitate by filtration, the filtrate was evaporated under reduced pressure. The residue was dissolved in water (10 ml), purified by column chromatography with use of Amberlite XAD-4 (Rohm and Haas Co.), and then treated with benzene to give 8.7 of crystalline 1-[1-(2-hydroxyethoxy)propyl]-5-fluorouracil.

m.p.: 111°–112° C.

NMR (DMSO-d$_6$)δ: 7.75 (1H,d,H-6), 5.75–5.45 (1H,m,

CH$_3$CH$_2$CH$\overset{O}{\underset{N}{<}}$), 3.85–3.40 (4H,m,HOCH$_2$CH$_2$O—), -continued 1.75 (2H,q,CH₃CH₂—), 0.95 (3H,t,CH₃CH₂—).

EXAMPLE 7

4-Ethyl-1,3-dioxolane (10 ml) prepared from butane-1,2-diol was added to bis(trimethylsilyl)-5-fluorouracil prepared from 5-fluorouracil (10 g) as in Example 1. To the mixture was added dropwise a solution of anhydrous stannic chloride (6 ml) in chloroform (15 ml) over one hour under cooling in an ice bath followed by stirring at room temperature for one hour. The reaction mixture was poured into methanol (100 ml) containing sodium bicarbonate (30 g), and after removing the resulting precipitate, the filtrate was evaporated under reduced pressure. The residue was dissolved in water (10 ml), purified by column chromatography with use of Amberlite XAD-4 (Rohm and Haas Co.), and treated with benzene to give 6.9 g of crystalline 1-(1-hydroxymethylpropyloxy)-methyl-5-fluorouracil.

m.p.: 76°–78° C.

NMR (CD₃OD)δ: 7.85 (1H,d,H-6), 5.22 (2H,S,CH₂ $\overset{O}{\underset{N}{\diagdown}}$ ), 3.52 (3H,bs,HOCH₂CH $\overset{C_2H_5}{\underset{O}{\diagdown}}$ ), 1.50 (2H,q, —CH₂CH₃), 0.9 (3H,t,—CH₂CH₃)

EXAMPLE 8

2-Phenyl-1,3-dioxolan (15 g) prepared from benzaldehyde and ethylene glycol was added to bis(trimethylsilyl)-5-fluorouracil prepared as in Example 1 from 5-fluorouracil (10 g). Then a solution of anhydrous stannic chloride (6 ml) in chloroform (15 ml) was added dropwise to the mixture over one hour while stirring under cooling in an ice bath. Following stirring at room temperature for one hour, the reaction mixture was poured into methanol (200 ml) containing sodium bicarbonate (40 g) followed by stirring at room temperature for one hour. The precipitate was removed by filtration and the filtrate was evaporated under reduced pressure to dryness. Acetic anhydride (20 ml) and pyridine (20 ml) were added to the residue and the mixture was left to stand at room temperature for 3 hours. The reaction mixture was poured into ice-water, and the resulting oil was extracted with chloroform (100 ml). The chloroform layer was washed with hydrochloric acid and then with water, and evaporated under reduced pressure to remove the solvent. The residue was purified by column chromatography using silica gel and chloroform as the eluent, and treated with methanol to give 6.3 g of crystalline 1-[α-(2-acetoxyethoxy)benzyl]-5-fluorouracil.

m.p.: 137.5°–139.5° C.

NMR (CDCl₃)δ: 7.40 (5H,S, ), 7.22 (1H,d,H-6), 6.89 (1H,d,—CH $\overset{O}{\underset{N}{\diagdown}}$ ), 4.45–4.20 (2H,m,CH₃

-continued

COOCH₂CH₂O—), 4.10–3.80 (2H,m,CH₃COOCH₂CH₂O—), 2.07 (3H,S,CH₃COO—).

EXAMPLE 9

Bis-trimethylsilyl-5-fluorouracil prepared from 5-fluorouracil (10 g) as in Example 1 was reacted with 2-(4-methoxyphenyl)-1,3-dioxolan prepared from p-methoxybenzaldehyde and ethylene glycol, and treated as in Example 8 to give 6.5 g of crystalline 1-[α-(2-hydroxyethoxy)-4-methoxybenzyl]-5-fluorouracil.

m.p.: 127°–132° C.

NMR (CDCl₃ + DMXO-d₆)δ: 7.36 (1H,d,H-6), 7.35, 6.88

(each 2H,d, 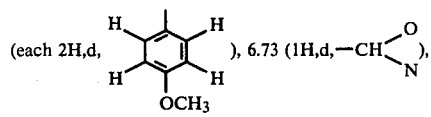), 6.73 (1H,d,—CH $\overset{O}{\underset{N}{\diagdown}}$ ), 3.78 (3H,S,O,CH₃), 3.71 (4H,bs,-, OCH₂CH₂O—).

EXAMPLE 10

Bis-trimethylsilyl-5-fluorouracil prepared as in Example 1 from 5-fluorouracil (10 g), and 2-(3,4-methylenedioxyphenyl)-1,3-dioxolan (18.1 g) prepared from piperonal and ethyleneglycol were dissolved in dichloromethane (50 ml). A solution of anhydrous stannic chloride (1 ml) in dichloromethane (10 ml) was added dropwise to the solution over one hour, and the mixture was stirred at room temperature overnight. Methanol (200 ml) containing sodium bicarbonate (30 g) was added to the reaction mixture and, after removing the precipitate by filtration, the filtrate was evaporated to dryness. Acetone (100 ml) was added to the residue and the undissolved material was removed by filtration. The filtrate was evaporated and the residue was purified by column chromatography using silica gel and chloroform-acetone (4:1) as an eluant.

The eluate was evaporated and the residue was treated with acetone-diisopropyl ether to give 6.3 g of crystalline 1-[α-(2-hydroxyethoxy)-3,4-methylenedioxybenzyl]-5-fluorouracil.

m.p.: 125°–129° C. (recrystallized from acetone-diisopropyl ether)

NMR (CDCl₃ + CD₃OD)δ: 7.37 (1H,d,H-6), 7.0–6.80 (3H, m, 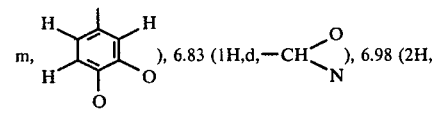), 6.83 (1H,d,—CH $\overset{O}{\underset{N}{\diagdown}}$ ), 6.98 (2H, S, ), 4.10–3.70 (4H,bs,HOCH₂CH₂O—).

EXAMPLE 11

1-[α-(2-Hydroxyethoxy)-3,4-methylendioxybenzyl]-5-fluorouracil obtained in Example 10 was dissolved in acetic anhydride (20 ml) and pyridine (20 ml) followed by stirring at room temperature for 3 hours. The reaction mixture was poured into ice-water and the resulting oil was extracted with chloroform (100 ml). The extract was washed with hydrochloric acid and then water, dried over magnesium sulfate and evaporated under reduced pressure to remove chloroform. The residue was treated with ligroinacetone to give 4.3 g of crystalline 1-[α-(2-acetoxyethoxy)-3,4-methylenedioxybenzyl]-5-fluorouracil.

m.p.: 131°–132° C. (recrystallized from methanol)

NMR (CDCl$_3$ + DMSO—d$_6$)δ: 7.24 (1H,d,H-6), 6.95–6.80

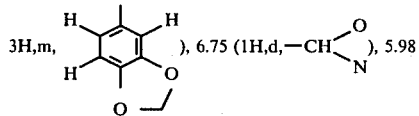), 6.75 (1H,d,—CH<O,N), 5.98

(2H,S, 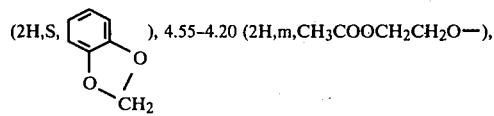), 4.55–4.20 (2H,m,CH$_3$COOCH$_2$CH$_2$O—), 4.0–3.75 (2H,m,CH$_3$COOCH$_2$CH$_2$O—), 3.08 (3H,S,CH$_3$COO—).

EXAMPLE 12

2-Hydroxygenzaldehyde (10 g) was dissolved in acetic anhydride (30 ml) and pyridine (30 ml) followed by stirring at room temperature for 3 hours. The reaction mixture was poured into ice-water and the resulting precipitate was recovered by filtration. The precipitate was dissolved in chloroform (100 ml), washed with water, dried and evaporated to give 2-acetoxybenzaldehyde. To a solution of 2-acetoxy-benzaldehyde (13 g) and ethyleneglycol (10 ml) in benzene (80 ml) was added Amberlist 15 (Rohm and Haas Co.) (3 g) and followed by refluxing for 5 hours. Water generated during refluxing was removed as an azeotropic mixture. The reaction mixture was washed with an aqueous solution of sodium bicarbonate, and then with water, and dried and evaporated. The residue was distilled under reduced pressure to collect a fraction distilled out at 115°–125° C./4 mmHg to give 10 g of 2-(2-acetoxyphenyl)-1,3-dioxolan. To a solution of 2-(2-acetoxyphenyl)-1,3-dioxolan (19.6 g) in dichloromethane (50 ml), bis(trimethylsilyl)-5-fluorouracil prepared as in Example 1 from 5-fluorouracil (10 g) was added and treated as in Example 10 to give 4.2 g of crystalline 1-[α-(2-hydroxyethoxy)-2-acetoxybenzyl]-5-fluorouracil.

m.p.: 165°–166.5° C. (recrystallized from isopropyl ether-dichloromethane)

NMR (CDCl$_3$ + CD$_3$OD)δ: 7.95–6.95 (5H,m,H-6,

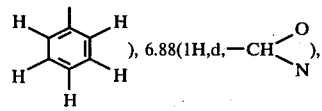), 6.88(1H,d,—CH<O,N), 3.74 (4H,S,HOCH$_2$—CH$_2$O—), 2.27 (3H,s,CH$_3$COO—).

EXAMPLE 13

4-Hydroxybenzaldehyde was acetylated with pyridine and acetic anhydride as in Example 12 to give 4-acetoxybenzaldehyde which was subjected to dehydration condensation with ethylene glycol to give 2-(4-acetoxyphenyl)-1,3-dioxolan. To a solution of 2-4-acetoxyphenyl)-1,3-dioxolan (13 g) in dichloromethane, bis(trimethylsilyl)-5-fluorouracil prepared as in Example 1 from 5-fluorouracil (10 g) was added followed by treating as in Example 10 to give 4.5 g of crystalline 1-[α-(2-hydroxyethoxy)-4-acetoxybenzyl]-5-fluorouracil.

m.p.: 144°–145.5° C. (recrystallized from isopropyl ether-ethanol)

NMR (CDCl$_3$ + DC$_3$OD)δ: 7.63–7.02 (5H, m,H-6,

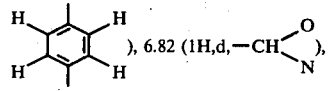), 6.82 (1H,d,—CH<O,N), 3.78(4H,S,HOCH$_2$CH$_2$O—), 2.29 (3H,s,CH$_3$COO—).

EXAMPLE 14

2-(3,4,5-Trimethoxyphenyl)-1,3-dioxolan (20.3 g) prepared from 3,4,5-trimethoxybenzaldehyde and ethylene glycol was dissolved in dichloromethane (50 ml). To the solution bis(trimethylsilyl)-5-fluorouracil prepared from 5-fluorouracil (10 g) was added and treated as in Example 10 to give 7.2 g of crystalline 1-[α-(2-hydroxyethoxy)-3,4,5-trimethoxybenzyl]-5-fluorouracil.

m.p.: 135.5°–138° C. (recrystallized from isopropyl ether-acetone)

NMR (CDCl$_3$ + CD$_3$OD)δ: 7.42 (1H,d,H-6), 6.72 (3H,bs,

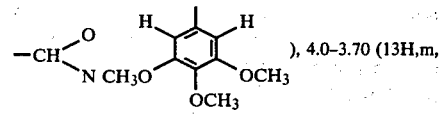), 4.0–3.70 (13H,m,

HOCH$_2$CH$_2$O—, OCH$_3$).

EXAMPLE 15

To the solution of 2-(3-methoxy-4-acetoxyphenyl)-1,3-dioxolan (22 g) prepared from 3-methoxy-4-hydroxybenzaldehyde as in Example 12 in dichloromethane (50 ml) bis(trimethylsilyl)-5-fluorouracil prepared from 5-fluorouracil (10 g) was added followed by treating as in Example 10 to give 9.8 g of crystalline 1-[α-(2-hydroxyethoxy)-3-methoxy-4-acetoxybenzyl]-5-fluorouracil.

m.p.: 130°–132.5° C. (recrystallized from isopropyl ether-chloromethane)

NMR (CDCl$_3$ + DMSO—d$_6$)δ: 7.30 (1H,d,H-6), 7.2–6.9 (3H,m,

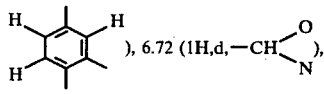), 6.72 (1H,d,—CH<O,N), 3.80 (4H,S,HOCH$_2$CH$_2$O—), 3.72 (3H,S,OCH$_3$), 2.26 (3H,S,CH$_3$CO—).

EXAMPLE 16

Uracil (10 g) was refluxed in hexamethyldisilazane for 5 hours and then distilled off excess hexamethyldisilazane. The resulting bis(trimethylsilyl)-uracil and 2-methyl-1,3-dioxolan (15 g) were dissolved in dichloromethane (50 ml) and treated as in Example 4 to give 4.4 g of crystalline 1-[alpha-(2-hydroxyethoxy)ethyl]uracil. m.p.: 124°–127° C.

NMR (DMSO—$d_6$)δ: 7.50, 5.58 (each 1H,d,H-5,H-6),

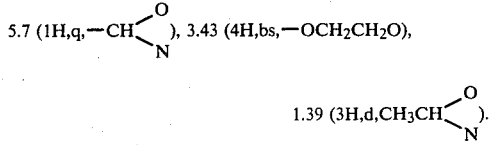

EXAMPLES 17–30

By the procedure similar to that in Example 10, compounds listed in the following Table 4 and Table 5 were prepared.

TABLE 4

| No. | $R_1$ | $R_2$ | $R_3$ | Yield (%) | m.p. (°C.) | NMR |
|---|---|---|---|---|---|---|
| 17 | cyclohexyl | H | H | 37 | 154–157.5 | CDCl$_3$ 7.46 (1H,d), 5.60–5.35 (1H,m), 3.9–3.5 (4H,m), 2.3–1.0 (11H,m) |
| 18 | CH$_3$O-phenyl- | H | H | 23 | 262–268 | CDCl$_3$ + DMSO - d$_6$ 7.26 (1H,d), 7.75–6.25 (4H,m), 3.5–3.9 (4H,m), 3.24 (3H,S) |
| 19 | —CH=CH—phenyl | H | H | 26 | 256–260 | CDCl$_3$ + CD$_3$OD 7.50 (1H,d), 7.31 (5H,d), 6.90 (1H,d), 6.45–6.30 (1H,m), 6.08 (1H,q), 3.73 (4H,S) |
| 20 | -phenyl-OC$_2$H$_5$ | H | H | 18 | 109–110 | CDCl$_3$ + DMSO - d$_6$ 7.41 (1H,d), 7.05 (4H,q), 6.62 (1H,m), 4.00 (2H,q), 3.66 (4H,S), 1.36 (3H,S) |
| 21 | CH$_3$(CH$_2$)$_{12}$— | H | H | 14 | 107–110 | CDCl$_3$ 7.46 (1H,d), 5.9–5.55 (1H,m), 3.9–3.45 (4H,m), 1.5–0.8 (27H,m) |
| 22 | 2,3-dimethoxyphenyl (CH$_3$O, OCH$_3$) | H | H | 13 | 134–136 | CDCl$_3$ + DMSO - d$_6$ 7.24 (1H,d), 7.4–6.95 (3H,m), 6.88 (1H,d), 3.85 (3H,S), 4.0–3.10 (7H,m) |
| 23 | -phenyl-CH(CH$_3$)$_2$ | H | H | 24 | 135–137 | CDCl$_3$ + DMSO - d$_6$ 7.6–7.1 (5H,m), 6.80 (1H,d), 3.78 (4H,b.s.), 3.2–2.5 (1H,m), 1.29, 1.18 (each 3H,S) |
| 24 | -phenyl-NO$_2$ | H | H | 14 | 173–175 | CDCl$_3$ + DMSO - d$_6$ 8.5–7.4 (4H,m), 7.59 (1H,d), 6.90 (1H,b.s.), 3.78 (4H,b.s.) |
| 25 | -phenyl-O(CH$_2$)$_3$CH$_3$ | H | H | 26 | 120–122 | CDCl$_3$ + DMSO - d$_6$ 7.45 (1H,d), 7.34, 6.86 (each 2H, d), 6.69 (1H,b.s.), 4.1–3.8 (2H, m), 3.8–3.6 (4H,b.s.), 1.9–0.8 (7H,m) |
| 26 | -phenyl-O(CH$_2$)$_5$CH$_3$ | H | H | 19 | 124–126 | CDCl$_3$ + DMSO - d$_6$ 7.44 (1H,d), 7.33, 6.86 (each 2H, d), 6.67 (1H,m), 4.1–3.8 (2H,m), 3.8–3.6 (4H,b.s.) 1.9–0.8 (11H,m) |

TABLE 4-continued

[Structure: 5-fluorouracil with N1-substituent CH2-O-CHR1-CHR2-OR3 on a dioxolane-like ring]

| No. | Compound R1 | R2 | R3 | Yield (%) | m.p. (°C.) | NMR |
|---|---|---|---|---|---|---|
| 27 | CH3-C6H4- (methylphenyl) | H | H | 30 | 165–169 | CDCl$_3$ + DMSO - d$_6$ 7.33 (1H,d), 7.7–7.1 (4H,m), 6.74 (1H,d), 3.78–3.42 (4H,m), 2.24 (3H,S) |
| 28 | 4-Cl-C6H4- | H | H | 30 | 169–171 | CDCl$_3$ + DMSO - d$_6$ 7.51 (1H,d), 7.43 (4H,S), 6.76 (1H,d), 3.69 (4H,b.s.) |

TABLE 5

[Structure: uracil with N1-substituent CH2-O-CHR1-CHR2-OR3]

| No. | Compounds R1 | R2 | R3 | Yield (%) | m.p. (°C.) | NMR |
|---|---|---|---|---|---|---|
| 29 | 2-(C2H5O)-C6H4- | H | H | 20 | 166–168 | CDCl$_3$ + DMSO - d$_6$ 7.15, 5.50 (each 1H,d), 6.8–7.8 (4H,m), 3.96 (2H,q), 3.60 (4H,S), 1.22 (3H,t) |
| 30 | 3,4-methylenedioxyphenyl- | H | H | 29 | 115–117 | CDCl$_3$ + DMSO - d$_6$ 7.19, 5.06 (each 1H,d), 6.6–6.95 (4H,m), 5.90 (2H,S), 3.80–3.50 (4H,b.s.) |

EXAMPLE 31

Bis(trimethylsilyl)5-fluorouracil prepared as in Example 1 from 5-fluorouracil (10 g), and 2-(2-ethoxyphenyl)-1,3-dioxolan (15 g) prepared from 2-ethoxybenzaldehyde and ethylene glycol were dissolved in dichloromethane (50 ml). The mixture was treated and acetylated as in Example 10 to give 6.2 g of crystalline 1-[α-(2-acetoxyethoxy)-2-ethoxybenzyl]-5-fluorouracil.

m.p.: 160°–165° C. (recrystallized from ethanol)

NMR (DMSO—d$_6$)δ: 7.7–6.6 (5H,m,H-6 and 2-ethoxyphenyl ring protons), 6.40 (1H,m,—CH(O)(N)—), 4.2–3.4 (6H,m,—OCH$_2$CH$_2$O—, OCH$_2$CH$_3$), 1.31 (3H,t,CH$_3$CH$_2$—).

EXAMPLE 32

To the solution of 1-[1-(2-hydroxyethoxy)-3-phenyl-2-propenyl]-5-fluorouracil (3 g) obtained in Example 19 in pyridine (10 ml), acetic anhydride (10 ml) was added followed by stirring at room temperature for 3 hours. The reaction mixture was poured into ice-water and extracted with chloroform. The chloroform layer was washed with water, dried and evaporated to remove chloroform. The residue was treated with a small amount of ethanol to give 2.8 g of crystalline 1-[1-(2-acetoxyethoxy)-3-phenyl-2-propenyl]-5-fluorouracil.

m.p.: 78°–81° C. (recrystallized from ethanol-isopropyl ether)

NMR (CDCl$_3$)δ: 7.5–7.2 (6H,m, phenyl and H-6), 6.88 (1H,

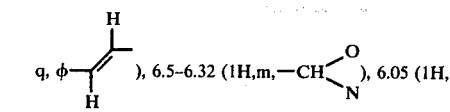

q, φ ), 6.5–6.32 (1H,m,—CH$<^O_N$), 6.05 (1H,

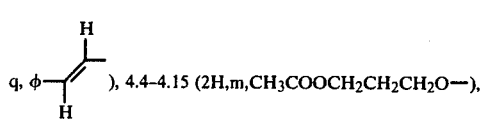

q, φ ), 4.4–4.15 (2H,m,CH₃COOCH₂CH₂CH₂O—), 3.85–3.70 (2H,m,CH₃COOCH₂CH₂O—), 2.06 (3H,S,CH₃COO—).

EXAMPLE 33

1-[α-(2-Hydroxyethoxy)-3,4-methylenedioxybenzyl-]uracil (3 g) obtained in Example 30 was added to pyridine (10 ml) and acetic anhydride (10 ml) followed by stirring at room temperature for 3 hours. The reaction mixture was poured into ice-water and the resulting oil was extracted with chloroform (30 ml). The chloroform layer was washed with water, dried and evaporated to remove the chloroform. The residue was treated with a small amount of ethanol to give 2.8 g of crystalline 1-[α-(2-acetoxy)-3,4-methylenedioxybenzyl]uracil.

m.p: 126°–128° C. (recrystallized from ethanol)

NMR (CDCl₃ + DMSO—d₆)δ: 7.14, 5.58 (each 1H,d,H-5,

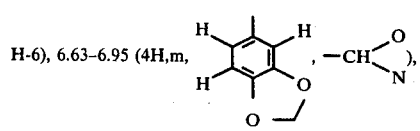

H-6), 6.63–6.95 (4H,m, , —CH$<^O_N$ ), 4.1–4.4 (2H,m,CH₃COOCH₂CH₂O—), 3.7–3.95 (2H,m,CH₃COOCH₂CH₂O—), 2.01 (3H,S,CH₃COO—).

EXAMPLE 34

Bis(trimethylsilyl)-5-fluorouracil prepared from 5-fluorouracil (10 g) , and 2-(3,4-diacetoxyphenyl)-1,3-dioxolan (26.6 g) prepared from 3,4-diacetoxybenzaldehyde and ethyleneglycol were treated as in Example 10 and the product was acetylated to give 7.4 g of crystalline 1-[α-(2-acetoxyethoxy)-3,4-diacetoxybenzyl]-5-fluorouracil.

m.p.: 184.5°–188° C.

NMR (CDCl₃ + DMSO—d₆)δ: 7.94 (1H,S,

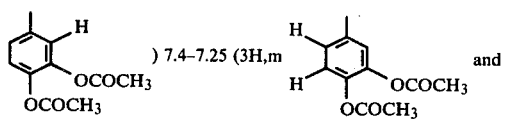

) 7.4–7.25 (3H,m and

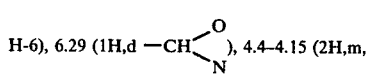

H-6), 6.29 (1H,d —CH$<^O_N$), 4.4–4.15 (2H,m,

CH₃COOCH₂CH₂O—), 4.0–3.25 (2H,m,CH₃COOCH₂CH₂O—),

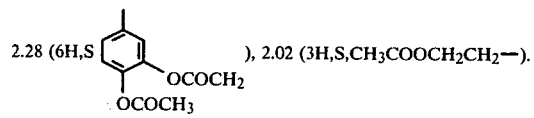

2.28 (6H,S ), 2.02 (3H,S,CH₃COOCH₂CH₂—).

EXAMPLE 35

Bis(trimethylsilyl)-5-fluorouracil prepared from 5-fluorouracil (10 g), and 2-2,6-dichlorophenyl-1,3-dioxolan (32.0 g) which had been prepared from 2,6-dichlorobenzaldehyde and ethylene glycol were subjected to reaction as in Example 10. Following adding chloroform (100 ml), the reaction mixture was washed twice with a cold saturated NaCl aqueous solution, and then aqueous sodium bicarbonate, and water, and dried over anhydrous magnesium sulfate. The solvent was evaporated off and the residue was purified by column chromatography using silica gel and acetone-chloroform (1:4) as an eluant to give 6.9 g of crystalline 1-[α-(2-hydroxyethoxy)-2,6-dichlorobenzyl]-5-fluorouracil.

m.p.: 163°–168° C.

NMR (CDCl₃ + DMSO—d₆)δ: 8.12 (1H,d,H-6), 7.30 (3H,

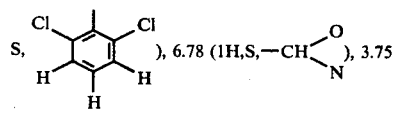

S, ), 6.78 (1H,S,—CH$<^O_N$), 3.75

(4H,b.s.—OCH₂CH₂O—).

EXAMPLE 36

Trimethylchlorosilane (4 ml) was added to a suspension of 5-methyluracil (thymine) (5 g) in hexamethylsilazane (20 ml) followed by refluxing for 5 hours. The resulting ammonium chloride was removed by filtration and the filtrate was evaporated to give bis(trimethylsilyl)-5-methyluracil as oil. To a solution of the oil in dry dichloromethane (10 ml) was added 2-methyl-1,3-dioxolane (15 ml) and then was added dropwise stannic chloride (5 ml). After allowing the mixture to stand at room temperature overnight, it was treated as in Example 10 to give 4.6 g of crystalline 1-[α-(2-hydroxyethoxy)-ethyl]-5-methyluracil.

m.p.: 149°–150° C. (recrystallized from ethanol)

NMR (d₆-DMSO)δ7.48 (1H,d), 5.94–5.55 (1H,q), 3.75–3.25 (4H,m), 1.80 (3H,S), 1.39 (3H,d)

EXAMPLES 37–47

By the procedure similar to that of Example 35, compounds listed in Table 6 were prepared.

TABLE 6

(Structure: 5-fluorouracil with N-substituted tetrahydrofuran bearing R₁, R₂, and OR₃ groups)

| No. | R₁ | R₂ | R₃ | Yield | m.p. (°C.) | NMR |
|---|---|---|---|---|---|---|
| 37 | —CH₂—C₆H₅ | H | H | 45 | 139–141 | CDCl₃:d₆-DMSO (1:1)<br>7.65 (1H,d), 7.19 (5H,S), 6.00–5.70 (1H,m), 3.51 (4H,b.s.), 3.22–2.95 (2H,m) |
| 38 | 3,4-(OCH₃)₂-C₆H₃— | H | H | 43 | 188–192 | CDCl₃:d₆-DMSO (1:1)<br>7.60–6.65 (4H,m), 6.54 (1H,S), 4.10–3.65 (4H,m), 3.80 (6H,S) |
| 39 | 2-(OCH₂CH=CH₂)-C₆H₄— | H | H | 49 | 130–135 | CDCl₃:d₆-DMSO (1:1)<br>7.80–6.75 (6H,m), 6.20–5.60 (1H,m), 5.55–5.00 (2H,m), 4.80–4.30 (2H,m), 3.69 (4H,b.s.) |
| 40 | 3-OCH₃-4-(OCH₂CH=CH₂)-C₆H₃— | H | H | 51 | — (oil) | CDCl₃:d₆-DMSO (4:1)<br>7.39 (1H,d), 7.1–6.90 (3H,m), 6.75 (1H,d), 6.45–5.70 (1H,m), 5.60–5.10 (3H,m), 4.80–4.50 (2H,m), 3.85 (3H,S), 3.73 (2H,b.s.) |
| 41 | naphthyl | H | H | 44 | 170–172 | CDCl₃:d₆-DMSO (4:1)<br>8.15–7.35 (7H,m), 7.26 (1H,d), 3.80 (4H,b.s.) |
| 42 | 4-(OCH₂CH=CH₂)-C₆H₄— | H | H | 47 | 177–180 | CDCl₃:d₆-DMSO (4:1)<br>7.95–6.65 (5H,m), 6.77 (1H,d), 6.40–5.70 (1H,m), 5.60–5.10 (2H,m), 4.65–4.45 (2H,m), 3.88 (4H,S) |
| 43 | 2-(COOC₂H₅)-C₆H₄— | H | H | 42 | 98–100 | CDCl₃<br>8.10–7.22 (5H,m), 7.16 (1H,d), 4.55–4.12 (2H,q), 3.81 (4H,b.s.), 1.52–1.15 (3H,t) |
| 44 | 3,4-(OCOCH₃)₂-C₆H₃— | H | H | 53 | 153–155 | CDCl₃<br>7.85–6.90 (4H,m), 6.76 (1H,d), 3.82 (2H,b.s.), 3.52 (2H,b.s.), 2.32 (3H,S), 2.29 (3H,S) |
| 45 | 3,4-(OCOC₂H₅)₂-C₆H₃— | H | H | 46 | 133–136 | CDCl₃:d₆-DMSO (4:1)<br>7.60–7.25 (4H,m), 6.83 (1H,d), 3.73 (4H,b.s.), 2.80–2.33 (4H,q), 1.40–1.02 (6H,t) |
| 46 | 3-OC₂H₅-4-OCOCH₃-C₆H₃— | H | H | 41 | 122–123 | CDCl₃:d₆-DMSO (1:1)<br>7.47 (1H,d), 7.70–6.90 (3H,d), 6.70 (1H,d), 4.30–3.85 (2H,q), 3.71 (4H,b.s.), 2.27 (3H,S), 1.05–1.20 (3H,t) |
| 47 | 3,4-(OCOC(CH₃)₃)₂-C₆H₃— | H | H | 40 | 176–178 | CDCl₃<br>7.42–7.13 (4H,m), 6.85 (1H,d), 3.78 (4H,b.s.), 1.32 (18H,S) |

EXAMPLES 48-60

By the procedure similar to that of Example 2 or 3, compounds listed in Table 7 were prepared.

TABLE 7

[Structure: 5-fluorouracil N-linked to a tetrahydrofuran ring bearing $R_3O$-CH$_2$-, $R_2$, and $R_3$ substituents]

| Compound No. | $R_1$ | $R_2$ | $R_3$ | Yield (%) | m.p. (°C) | NMR |
|---|---|---|---|---|---|---|
| 48 | 3,4-(OCH$_3$)(OCOCH$_3$)-phenyl | H | CH$_3$CO | 70 | 67-75 | CDCl$_3$ 7.22(1H, d), 7.02(3H, S), 6.82(1H, d), 4.44-4.20(2H, m), 4.03-3.75 (2H, m), 3.82(3H, S), 2.30(3H, S), 2.05(3H, S) |
| 49 | 3,4-methylenedioxyphenyl | H | CH$_3$SO$_2$ | 75 | 133-134 | CDCl$_3$: d$_6$-DMSO (4:1) 7.02 (1H, d), 6.68(3H, d), 6.55(1H, d), 5.80(2H, S), 4.40-4.15(2H, m), 3.90-3.55(2H, m), 2.90(3H, S) |
| 50 | 2-OCOCH$_3$-phenyl | H | CH$_3$CO | 82 | 80-87 | CDCl$_3$ 7.8-6.95(5H, m), 6.86(1H, d), 4.42-4.18(2H, m), 4.02-3.75(2H, m), 2.25(3H, S), 2.02(3H, S) |
| 51 | 4-OCOCH$_3$-phenyl | H | CH$_3$CO | 74 | 94-95 | CDCl$_3$ 7.60-7.02(5H, m), 6.86(1H, d), 4.45-4.20(2H, m), 4.02-3.78(2H, m), 2.28(3H, S), 2.04(3H, S) |
| 52 | 3,4-di(OCOCH$_3$)-phenyl | H | CH$_3$CO | 77 | 140-144 | CDCl$_3$ 8.12-7.60(1H, q), 7.20(1H, d), 6.80-7.12(2H, m), 6.75(1H, d), 4.40-4.10 (2H, m), 4.02-3.70(2H, m), 2.23(3H, S), 2.15(3H, S), 2.00(3H, S) |
| 53 | 3-OCOCH$_3$-phenyl | H | CH$_3$CO | 71 | 123-125 | CDCl$_3$ 7.50-7.00(5H, m), 6.87(1H, d), 4.45-4.20(2H, m), 4.05-3.75(2H, m), 2.29(3H, S), 2.05(3H, S) |
| 54 | 3,4-di(OC$_2$H$_5$)-phenyl | H | CH$_3$CO | 80 | 180-185 | CDCl$_3$ 7.12(1H, d), 6.83(3H, S), 6.72(1H, d), 4.39-3.79(8H, m), 1.04(3H, S), 1.62-1.29(3H, t) |
| 55 | 3,4-di(OCO(CH$_2$)$_2$CH$_3$)-phenyl | H | CH$_3$CO— | 79 | 131-132 | CDCl$_3$ 7.16(3H, b.s.), 7.13(1H, d), 6.78 (1H, d), 4.45-4.10(2H, m), 4.00-3.75 (2H, m), 1.75-2.35(4H, t), 2.04(3H, S), 2.00-1.35(4H, q), 1.30-0.93 6H, t) |
| 56 | 3,4-di(OCOCH(CH$_3$)$_2$)-phenyl | H | CH$_3$CO— | 73 | 129-133 | CDCl$_3$ 7.19(3H, S), 7.13(1H, d), 6.28(1H, d), 4.41-4.16(2H, m), 4.03-3.75 (2H, m), 3.08-2.51(1H, m), 2.02 (3H, S), 1.36(6H, S), 1.24(6H, S) |
| 57 | 3,4-di(OCOCH$_3$)-phenyl | H | —COC(CH$_3$)$_3$ | 71 | 118-120 | CDCl$_3$ 7.30(3H, S), 7.22(1H, d), 6.90(1H, d), 4.50-4.20(2H, m), 4.60-3.75 (2H, m), 2.29(6H, S), 1.19(9H, S) |

TABLE 7-continued

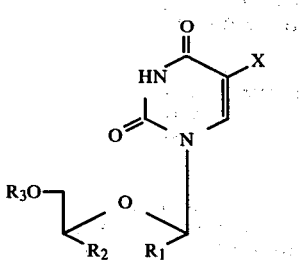

| No. | R₁ | R₂ | R₃ | Yield (%) | m.p. (°C.) | NMR |
|---|---|---|---|---|---|---|
| 58 | ![OCO(CH₂)₃CH₃ phenyl di-substituted] | H | CH₃CO— | 72 | 115-116 | CDCl₃ 7.30(3H, S), 7.25(1H, d), 6.90(1H, d), 4.50-4.15(2H, m), 4.05-3.80 (2H, m), 2.75-2.35(4H, t), 2.07 (3H, S), 2.00-0.75(14H, m) |
| 59 | ![OCH₃ / OCOC(CH₃)₃ phenyl] | H | CH₃CO | 74 | 95-96 | CDCl₃ 7.22(1H, d), 7.03(3H, S), 6.87(1H, d), 4.50-4.22(2H, m), 4.10-3.80 (2H, m), 3.82(3H, S), 2.05(3H, S), 1.34(9H, S) |
| 60 | ![O-CH₂/O phenyl methylenedioxy] | H | —COC(CH₃)₃ | 76 | 137-138 | CDCl₃ 7.21(1H, d), 7.0-6.70(3H, m), 6.00(2H, S), 4.85-4.20(2H, m), 4.05-3.70(2H, m), 1.19(9H, S) |

What is claimed is:

1. An uracil derivative of the formula

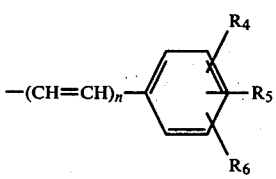

wherein R₁ is a hydrogen atom, an alkyl group of 1-14 carbons, a cycloalkyl group of 3-8 carbons or —(CH=CH)ₙ—⟨phenyl with R₄, R₅, R₆⟩

(wherein n is 0 or 1; R₄, R₅ and R₆ are the same or different and means a hydrogen atom, an alkyl group of 1-5 carbons, an alkoxy group of 1-6 carbons, an alkenyloxy group, a hydroxy group, an acyloxy group of 2-4 carbons, a halogen atom or a nitro group; and two of R₄, R₅ and R₆ may be taken together to form an alkylene dioxy group); R₂ is a hydrogen atom or an alkyl group of 1-5 carbons; R₃ is a hydrogen atom, an acyl group of 1-5 carbons, an unsubstituted or alkyl-substituted phenylsulfonyl group or an alkylsulfonyl group; and X is a hydrogen atom, a halogen atom or an alkyl group of 1-4 carbons which may be substituted with one or more halogen atoms, provided that when X is an alkyl, all of R₁, R₂ and R₃ are not a hydrogen atom simultaneously or two of said R₁, R₂, and R₃ are not hydrogen while a third is methyl simultaneously; and pharamaceutically acceptable salts thereof.

2. An uracil derivative of the formula

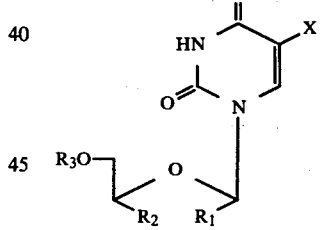 wherein R₁ is 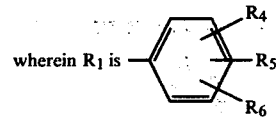

(wherein R₄, R₅ and R₆ are the same or different and mean an alkoxy group of 1-6 carbons or an acyloxy group of 2-4 carbons; and two of R₄, R₅ and R₆ may be taken together to form an alkylene dioxy group); R₂ is a hydrogen atom; R₃ is a hydrogen atom or an acyl group of 1-5 carbons; X is a halogen atom; and pharmaceutically acceptable salts thereof.

3. A process for preparing an uracil derivative according to claim 1 which comprises reacting an acetal of the formula

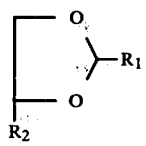

(wherein R₁ and R₂ are as defined above) with an uracil compound of the formula

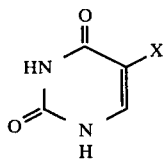

or its trialkylsilyl ether in the presence of a Lewis acid in an organic solvent selected from dichloromethane, chloroform, dimethylformamide or dimethylacetamide; said Lewis acid being selected from anhydrous stannic chloride, titanium tetrachloride, boron trifluoride, zinc chloride, aluminum chloride or ethyl aluminum chloride; said reaction being carried out at from −10° to 100° C. for 0.5 to 50 hours; and optionally acylating the hydroxy group of the reaction product.

4. A process according to claim 3 wherein the amount of said Lewis acid ranges from 0.1 to 1.0 moles per mole of the uracil compound.

5. A process according to claim 3 wherein said reaction is carried out at from 20° to 50° C. for 1 to 12 hours.

6. A pharmaceutical anti-tumor composition comprising an anti-tumor effective amount of an uracil derivative or its pharmaceutically acceptable salt according to claim 1 and a pharmaceutically acceptable diluent.

7. A pharmaceutical composition according to claim 6 wherein the composition is formulated in the form for oral administration selected from tablet, granule, powder or capsule.

8. A pharmaceutical composition according to claim 7 wherein the diluent used for the formulation is selected from lactose, starch, dextrin, sucrose, crystalline cellulose, kaolin, calcium carbonate, talc or magnesium stearate.

9. A pharmaceutical composition according to claim 6 wherein the composition is formulated in the form of injection.

10. A pharmaceutical composition according to claim 9 wherein said injection is formulated with use of distilled water or a sodium chloride or potassium chloride aqueous solution.

* * * * *